(12) United States Patent
Prosser

(10) Patent No.: US 11,000,704 B2
(45) Date of Patent: May 11, 2021

(54) MANAGING RADIOTHERAPY SYSTEMS

(71) Applicant: Elekta Limited, West Sussex (GB)

(72) Inventor: Timothy Prosser, Atlanta, GA (US)

(73) Assignee: Elekta Limited, West Sussex (GB)

(*) Notice: Subject to any disclaimer, the term of this patent is extended or adjusted under 35 U.S.C. 154(b) by 0 days.

(21) Appl. No.: 16/843,303

(22) Filed: Apr. 8, 2020

(65) Prior Publication Data

US 2020/0230440 A1 Jul. 23, 2020

Related U.S. Application Data

(63) Continuation of application No. 15/349,472, filed on Nov. 11, 2016, now Pat. No. 10,653,894.

(30) Foreign Application Priority Data

Nov. 25, 2015 (GB) .................................... 1520823

(51) Int. Cl.
    *A61N 5/10* (2006.01)

(52) U.S. Cl.
    CPC ........... *A61N 5/1075* (2013.01); *A61N 5/103* (2013.01); *A61N 5/1045* (2013.01);
    (Continued)

(58) Field of Classification Search
    CPC ............ A61N 2005/1074; A61N 5/103; A61N 5/1045; A61N 5/1048; A61N 5/1075; A61N 5/1081
    See application file for complete search history.

(56) References Cited

U.S. PATENT DOCUMENTS

| 5,511,549 A | 4/1996 | Legg et al. |
| 10,653,894 B2 * | 5/2020 | Prosser ................ A61N 5/1048 |

(Continued)

FOREIGN PATENT DOCUMENTS

| EP | 0 809 525 A1 | 12/1997 |
| GB | 2 344 985 A | 6/2000 |

(Continued)

OTHER PUBLICATIONS

Great Britain Search Report issued in Patent Application No. GB1520823.4, dated May 6, 2016, 4 pages.

(Continued)

*Primary Examiner* — Chih-Cheng Kao
(74) *Attorney, Agent, or Firm* — Finnegan, Henderson, Farabow, Garrett & Dunner LLP

(57) ABSTRACT

Embodiments disclose methods and apparatus for managing the provision of radiotherapy treatment. The method includes storing a database of calibration settings for a plurality of components of a first radiotherapy system. The calibration settings may be used by the first radiotherapy system to translate treatment plans into instructions for the plurality of components to carry out. The method further includes deriving from the database allowable ranges of values for the calibration settings. The method also includes receiving from a second radiotherapy system calibration settings for the second radiotherapy system prior to implementation of a treatment plan, comparing the calibration settings for the second radiotherapy system with the derived allowable ranges of values, and generating an alert signal when a subset of the calibration settings for the second radiotherapy system falls outside the allowable range of values.

20 Claims, 3 Drawing Sheets

(52) U.S. Cl.
CPC ......... *A61N 5/1048* (2013.01); *A61N 5/1081* (2013.01); *A61N 2005/1074* (2013.01)

(56) References Cited

U.S. PATENT DOCUMENTS

| | | | |
|---|---|---|---|
| 2004/0164254 A1 * | 8/2004 | Beloussov | A61N 5/1079 250/492.1 |
| 2010/0082294 A1 | 4/2010 | Adnani | |
| 2010/0117002 A1 | 5/2010 | Rinecker et al. | |
| 2013/0048883 A1 | 2/2013 | Simon et al. | |
| 2013/0289332 A1 | 10/2013 | Purdie et al. | |
| 2015/0251021 A1 | 9/2015 | Boisseau et al. | |

FOREIGN PATENT DOCUMENTS

| | | |
|---|---|---|
| WO | WO 2012/171538 A1 | 12/2012 |
| WO | WO 2014/035419 A1 | 3/2014 |

OTHER PUBLICATIONS

European Search Report issued in Patent Application No. EP 16 19 9601.2, dated Mar. 22, 2017, 8 pages.

* cited by examiner

MANAGING RADIOTHERAPY SYSTEMS

CROSS REFERENCE TO RELATED APPLICATIONS

This application is a continuation of U.S. patent application Ser. No. 15/349,472 filed Nov. 11, 2016 (now allowed), which claims the benefit and priority of prior United Kingdom Patent Application No. GB 1520823.4, filed on Nov. 25, 2015. The disclosures of the above-referenced applications are all expressly incorporated by reference herein.

TECHNICAL FIELD

The present disclosure relates to methods and apparatus for managing radiotherapy systems, and particularly to methods and apparatus for ensuring that radiotherapy systems deliver safe treatment.

BACKGROUND

Prior to beginning a course of radiotherapy, a plan for the treatment is generated. The aim of the treatment plan is to establish how to apply the radiotherapy to the patient so that the target region receives the desired, therapeutic dose, whilst the surrounding healthy tissue receives as little dose as possible.

The process of treatment planning is complex and time-consuming. It involves first acquiring an image of the patient ("the planning image") which contains at least the region which is targeted for treatment as well as the surrounding area. A clinician reviews the image and specifies maximum and minimum doses for different regions shown in the image. For example, the target region may be assigned a minimum dose the target region should receive a dose of at least X), while sensitive healthy regions near the target region may be assigned a maximum dose this sensitive region should receive a dose of no more than Y). This three-dimensional map is then used to generate a treatment plan which specifies the dose to be administered to the patient and the angle at which that dose is to be applied from, Typically each treatment plan will consist of multiple doses from multiple directions, or "arcs".

The generation of the treatment plan can be expressed as a mathematical problem in which the overall dose to healthy tissue must be minimized, subject to constraints as to the maximum dose to be delivered to sensitive regions (such as healthy organs, for example) and the minimum dose to be delivered to target regions. Although complex, the problem can be solved using significant computing resources and one of various techniques known to those skilled in the art.

The treatment plan so generated does not always produce an optimal clinical outcome. Therefore, every treatment plan is reviewed by a clinician to check that it delivers an acceptable dose profile to the patient. If not, a further iteration of the process receives the feedback from the clinician and generates an updated treatment plan. This process can be repeated as many times as necessary until an acceptable treatment plan is created.

The treatment plan is then passed to the radiotherapy system to be implemented, delivering targeted radiation to a patient in order to treat some medical condition. The treatment plan merely specifies the dosage to be delivered to the patient and the direction the dosage is to be applied from, however. Although useful from a clinical point of view, such information does not specify the voltage to be applied in the linear accelerator to generate the therapeutic radiation; it does not specify the length of time power should be supplied to the rotatable gantry in order to move the radiation head through a certain range. In short, it does not specify the actual instructions to be input to the radiotherapy system to put the treatment plan into effect. In order to translate the information in the treatment plan into useful instructions for the various components of the system (and there are many such components); the radiotherapy system requires a calibration data set which converts the treatment plan dosage instructions into practical instructions for the components.

The calibration data set is generally stored locally to the radiotherapy system, and may be amended over time to account for changes to the radiotherapy system itself. Components of the system may be upgraded, or new components added (e.g. new collimation apparatus). Conversely, the performance of existing components may degrade over time. By appropriate maintenance of the calibration settings for these components, the performance of the system as a whole can be maintained at a consistent level over a prolonged period of time.

As noted above, the calibration data sets for radiotherapy systems are typically stored locally. Furthermore, they are also generally updated manually. For example, a technician may review and update the calibration data set as part of a regular maintenance schedule. Additionally, or alternatively, the technician may update the calibration data set only when some maintenance is carried out on the system (e.g. installation or replacement of system components).

This manual entry of calibration data can lead to problems. For example, if the calibration data set contains an error through a typographic or otherwise erroneous entry of data), the treatment delivered to the patient may not conform to the dosage profile that was predicted when the treatment plan was generated and approved by a clinician. At the same time, however, it is beneficial to allow a degree of flexibility to the technicians maintaining the calibration data sets, to allow radiotherapy systems to be operated for longer and otherwise to account for minor variations between each system.

SUMMARY

According to a first embodiment of the present disclosure, there is provided a method of managing radiotherapy systems. The method includes storing a database of calibration settings for a plurality of components of a first radiotherapy system. The calibration settings may be used by the first radiotherapy system to translate treatment plans into instructions for the plurality of components to carry out, deriving from the database allowable ranges of values for the calibration settings. The method may further include receiving from a second radiotherapy system calibration settings for the second radiotherapy system prior to implementation of a treatment plan, comparing the calibration settings for the second radiotherapy system with the derived allowable ranges of values, and generating an alert signal when a subset of the calibration settings for the second radiotherapy system falls outside the allowable range of values.

According to a second embodiment of the present disclosure, there is provided a method of operating a radiotherapy system, the radiotherapy system comprising a memory and a plurality of operational components for delivery of therapeutic radiation to a patient, the memory storing a calibration data set comprising respective calibration settings for the plurality of operational components, said calibration settings being used by the radiotherapy system to translate radiotherapy treatment plans into instructions for the plurality of operational components, the method comprising: prior to implementation of a treatment plan, transmitting the calibration data set for the radiotherapy system to a management apparatus, the management apparatus comprising a database of calibration data sets and a respective allowable range for the calibration settings; and receiving an alert signal from the management apparatus if a subset of the calibration settings fall outside their respective allowable ranges.

Each of these methods may be embodied in a computer-readable medium storing program code which, when executed, cause the methods to be carried out.

According to a third embodiment of the present disclosure, there is provided an radiotherapy management apparatus. The radiotherapy management apparatus includes a storage device that stores a set of instructions and a database of calibration settings for a plurality of components of a first radiotherapy system. The calibration settings may be used by the first radiotherapy system to translate treatment plans into instructions for the plurality of components to carry out. The radiotherapy management system may further include a processor coupled to the storage device. The processor may execute the set of instructions to perform operations including deriving from the database allowable ranges of values for the calibration settings, receiving from a second radiotherapy system calibration settings for the second radiotherapy system prior to implementation of a treatment plan, comparing the calibration settings for the second radiotherapy system with the derived allowable ranges of values, determining whether a subset of the calibration settings falls outside the derived allowable ranges of values, and generating an alert signal based on the determination.

BRIEF DESCRIPTION OF DRAWINGS

For a better understanding of the present disclosure, and to show more clearly how it may be carried into effect, reference will now be made, by way of example, to the following drawings, in which.

DETAILED DESCRIPTION

Figure 1:
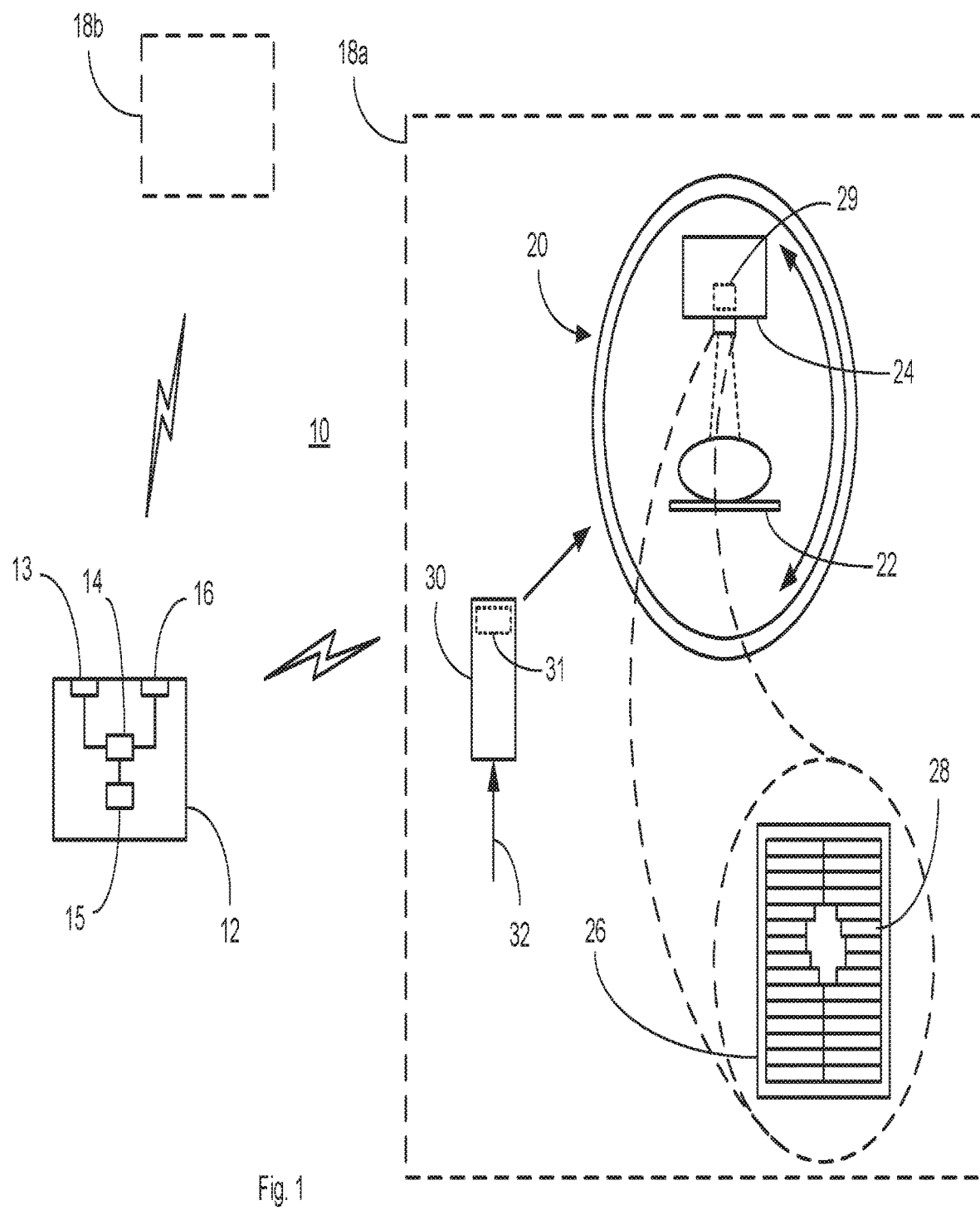
FIG. 1 shows an example of a radiotherapy system according to embodiments of the present disclosure.

FIG. 1 shows a system 10 according to embodiments of the present disclosure. The system comprises a radiotherapy management apparatus 12 and a plurality of radiotherapy systems 18a, 18b. Each radiotherapy system is located in its operative environment; for example in the oncology department of a hospital. Each hospital may possess more than one radiotherapy system, but in general it is assumed the radiotherapy systems are in separate hospitals, potentially distributed around the world. It is further to be understood that, although only two radiotherapy systems are illustrated in FIG. 1, the system according to embodiments of the present disclosure may (and generally will) comprise many such radiotherapy systems. The management apparatus 12 is able to communicate with each radiotherapy system 18a, 18b, either by wired or wireless communications, or by a combination of both wired and wireless communications through, for example, a network such as the Internet. The apparatus 12 comprises an input 13, for receiving communications from the radiotherapy systems 18a, 18b, and an output 16, for sending communications to the radiotherapy systems 18a, 18b, A processor 14 is coupled to the input 13 and the output 16, and further has access to a memory 15. The operation of the management apparatus 12 will be described in greater detail below. The memory 15 will generally be non-volatile memory. The memory may store a database of calibration data sets, and additionally a set of instructions to be carried out by the processor 14 in order to implement the methods set out below.

The management apparatus 12 itself may be local or remote to the radiotherapy systems 18a, 18b. For example, as illustrated, the system 10 may comprise a single management apparatus 12 with which each radiotherapy system communicates as necessary. Alternatively, the system may comprise a plurality of such management apparatuses, each able to access a central database (or periodically updating the contents of a local database based on the contents of a central database).

The system 18a comprises a radiotherapy apparatus 20 in which a patient is supported by a suitable support apparatus 22. The radiotherapy apparatus 20 is operative under the control of a control device 30, which is a computing device comprising at least one or more processors and memory. A radiation head 24 comprises a source of ionizing radiation (e.g. x-rays, electrons, protons, etc.) having sufficient energy to produce a therapeutic effect in the patient (i.e. generally in the megavoltage range), and a collimating device to collimate that radiation into a beam of desired shape. In operation, the radiation head 24 is able to rotate around the patient such that the radiation beam is directed towards a target region in the patient as from a number of different angles. By positioning the target region at or near the rotation axis of the head 24, the radiation beam intersects the target region throughout rotation of the head, but passes through the surrounding tissue only momentarily. In this way, collateral damage to healthy tissue as a result of the treatment can be reduced.

The dashed-line projection in FIG. 1 shows a beam's eye view of the collimating device in operation. A housing 26 defines a radiation field through which the radiation beam passes. In the illustrated embodiment, two banks of opposing leaves 28 are coupled to the housing 26 and extend across the radiation field to a greater or lesser extent as required. Each leaf is relatively thin in one direction, but relatively long in its direction of travel across the radiation field, and relatively deep in a direction parallel to the radiation beam axis (i.e. into the page in FIG. 1). The depth of the leaf; together with the choice of a manufacturing material having high atomic number (such as tungsten), acts to effectively block that part of the radiation field, preventing radiation from passing through. Each leaf is individually controllable to take any position in the range from falling outside the radiation field to extending fully across the radiation field; and thus the plurality of leaves can be controlled to define collectively a radiation beam having a desired cross-sectional shape (for example, to match the shape of a tumour or other target within the patient). This type of device is known as a multi-leaf collimator (MLC), Other collimating devices are known, however (such as binary collimators and block collimators), and the present disclosure is equally applicable to radiotherapy systems employing these types of devices. The radiotherapy systems may employ more than one collimating device.

The system 18a may further comprise one or more devices 29 for monitoring the beam energy and/or the beam current. For example, a monitor chamber may be used as a safety device to check the energy of the radiation beam, the radiation beam current (where the beam is formed with charged particles) and/or the intensity of the radiation beam, and so ascertain whether those parameters conform to expected values, or within expected ranges.

It will be apparent to the reader and to those skilled in the art that each course of radiotherapy involves control of a huge number of variables. Depending on the type of radiotherapy system employed, the variables may include: rotation angle of the radiation head; positions of the MLC leaves (or other collimating elements); energy of the beam; overall amount of radiation dose being delivered (i.e. the number of monitor units); rate of delivery of that dose; position of the "wedge" (an absorptive collimating element used to reduce skin dose in some methods of treatment); the type of treatment being delivered (e.g. electron therapy or x-ray therapy, etc.); and the patient position. Thus, there are a large number of variables offered by the apparatus in order to tailor the radiation dose that is delivered to the patient. A treatment plan is therefore required to control the radiotherapy apparatus 20 to provide a desired level of radiation dose to the patient.

As part of the treatment planning process, volumetric images of the patient are analysed to identify a target region into which a minimum dose is to be delivered, any sensitive regions such as functional organs for which a maximum dose must be observed, and other non-target regions into which the dose is to be generally minimised. This three-dimensional map is then used to develop a treatment plan 32, i.e. a sequence of source movements, collimator shapes, and dose rates which result in a three-dimensional dose distribution that (a) meets the requirements as to maximum and minimum doses (etc.) and (b) is physically possible, e.g. does not require the source to rotate around the patient faster than it is physically capable.

In use, the treatment plan 32 is passed to the control apparatus 30 to be implemented in the radiotherapy system 20. However, although useful from a clinical point of view, the treatment plan 32 does not specify the practical inputs required to bring about the dosage rates, etc. specified in the treatment plan. It does not specify the actual instructions which are input to the radiotherapy system to put the treatment plan into effect. In order to translate the information in the treatment plan into useful instructions for the various components of the system, the control apparatus 30 comprises a memory 31 which stores a calibration data set for converting the treatment plan dosage instructions into practical instructions for the components of the radiotherapy system. The memory 31 may additionally comprise a set of computer-readable instructions to be carried out by the control device 30 in order to implement the methods set out below.

For each of the various components of the radiotherapy system, the calibration data set may comprise one or more calibration settings which specify what input is required to achieve a particular output. The control apparatus 30 thus takes a treatment plan 32 as an input; applies the calibration settings specified in the calibration data set, and generates a plurality of instructions for the radiotherapy system 20 to implement the treatment plan 32.

For example, the calibration data set may include calibration settings (e.g. coefficients) for the rotatable gantry, specifying what voltage must be applied to the motor rotating the gantry in order to achieve a particular rate of rotation; if different rates of rotation are not available, the setting may specify how long the motor ought to be operated in order to achieve a particular rotation of the gantry. The calibration data set may include one or more calibration settings specifying what voltage should be applied to the source of radiation in order to achieve a desired energy in the radiation beam; or the frequency of pulsing of the radiation beam. The calibration data set may include calibration settings for the one or more collimator devices of the radiotherapy apparatus 20, incorporating the number and dimensions of the collimating elements of those devices, so as to enable a radiation beam shape specified in the treatment plan to be implemented. The calibration data set may include one or more calibration settings for beam monitor devices monitor chambers); for example, such settings may comprise a voltage to be applied to the monitor devices so as to measure accurately beam energy, beam current, and/or beam intensity.

Figure 2:
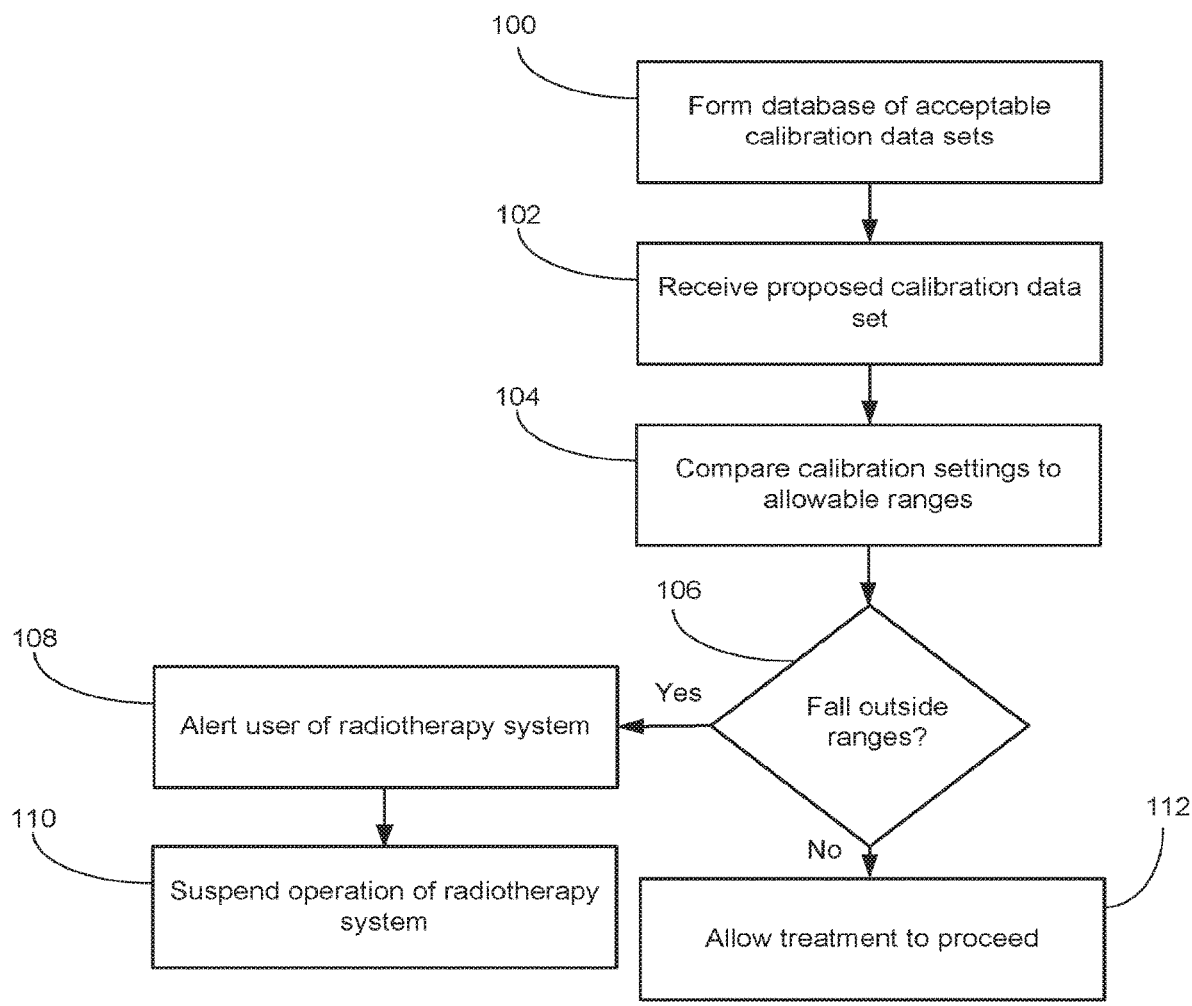
FIG. 2 is a flowchart of a method according to embodiments of the present disclosure.

The radiotherapy system assigned reference numeral 18a is an example of the type of radiotherapy apparatus which may be employed in methods according to the present disclosure. It will be apparent to those skilled in the art that the present disclosure is applicable to multiple different types of radiotherapy system having some, none, or all features in common with system 18a. For example, the source of radiation may be able to rotate around the patient (such as in system 18a), or may be fixed at a particular orientation with respect to the patient. The source of radiation may produce the same, or different ionizing radiation, or be capable of producing multiple types of ionizing radiation. One or multiple collimating devices may be employed, and these could be multi-leaf collimators, block collimators, binary collimators or any other collimating device. The detail of system 18b is not shown for clarity, but it may therefore be the same as or different to system 18a. In general, the system 18b comprises at least a control apparatus and a radiotherapy apparatus comprising a source of radiation, FIG. 2 is a flow chart of a method according to embodiments of the disclosure, carried out in the management apparatus 12.

In step 100, a database is formed of calibration data sets which have been found to deliver acceptable treatments, i.e. the levels of radiation dose generated by the radiotherapy systems employing those calibration data sets have been found to conform to those specified in the treatment plans. As explained above, each calibration data set comprises one or more calibration settings (or coefficients) for a number of components, including one or more of: the motor controlling rotation of the gantry; the MLC leaves (or other collimating elements); beam monitor devices; the source of radiation. The database is then stored in memory 15.

The database can be used to derive allowable ranges of values for each of the settings of the calibration data set. An allowable range may simply be the presence of values for a particular setting. For example, if a calibration data set failed to include any settings for a component that is present in the radiotherapy apparatus it is to be implemented in, it is possible that the apparatus could deliver an excessive dose of radiation (or an inaccurate dose of radiation). For other parameters, the allowable range may be a range of values. For example, an upper limit may be placed on the calibration setting for the pulse frequency and/or the energy of the source of radiation, to avoid excessively high frequencies or beam energies. The allowable ranges may be derived relative to average values for the calibration settings in question. For example, if the average value for a particular calibration setting across the calibration data sets in the database is Y, the allowable range may be defined as Y−50% to Y+50%. Alternatively, absolute values may be used to define the allowable range relative to the average value. The database may be formed and updated over a period of time, in a manner to be explained below, or generated by an appropriately trained and qualified clinician.

In step 102, the management apparatus 12 receives at its input 13 a proposed calibration data set from a radiotherapy system 18a, 18b, prior to the implementation of a treatment plan using the proposed calibration data set. Thus, a patient has been admitted to hospital for radiotherapy. Various images of the treatment area have been acquired and a treatment plan has been drawn up. The treatment plan is about to be implemented in the radiotherapy system, using the calibration data set. In embodiments of the present disclosure, the calibration data set is transmitted to the management apparatus 12 as the treatment plan 32 plan is loaded into the control apparatus 30 for execution, i.e. in real time, just before the patient is to undergo therapy.

The proposed calibration data set comprises values for a plurality of calibration settings, and thus in step 104, the comparison logic 14 compares the values for each calibration setting to the corresponding allowable range derived in step 100.

Step 106 is a decision step of whether a predetermined number of the calibration settings of the proposed calibration data set fall outside the allowable ranges. In an embodiment of the present disclosure, the predetermined number is one; in other embodiments, the predetermined number may be user defined, and equal to a value more than one.

If the outcome of the decision step 106 is positive, the comparison logic generates an appropriate message and transmits it to the radiotherapy system 18a, 18b via the output 16. The message may be an alert for display to the user (i.e. a technician) of the radiotherapy apparatus (step 108), or an instruction to the radiotherapy apparatus itself to suspend operation (step 110), or both. Patient safety is enhanced in either case.

If the decision step 106 results in a negative determination (i.e. the calibration settings are all within the allowable ranges or fewer than the predetermined number of calibration settings are outside the allowable ranges), the treatment is allowed to proceed (step 112). The comparison logic 14 generates an appropriate message, and transmits it to the radiotherapy system 18a via output 16.

According to embodiments of the present disclosure, once the proposed calibration data set has been deemed safe in this way, its calibration settings may be added to the database such that the allowable ranges can be updated if necessary. In this way, the database can constantly evolve as new treatments are deemed safe and as technology progresses.

Figure 3:
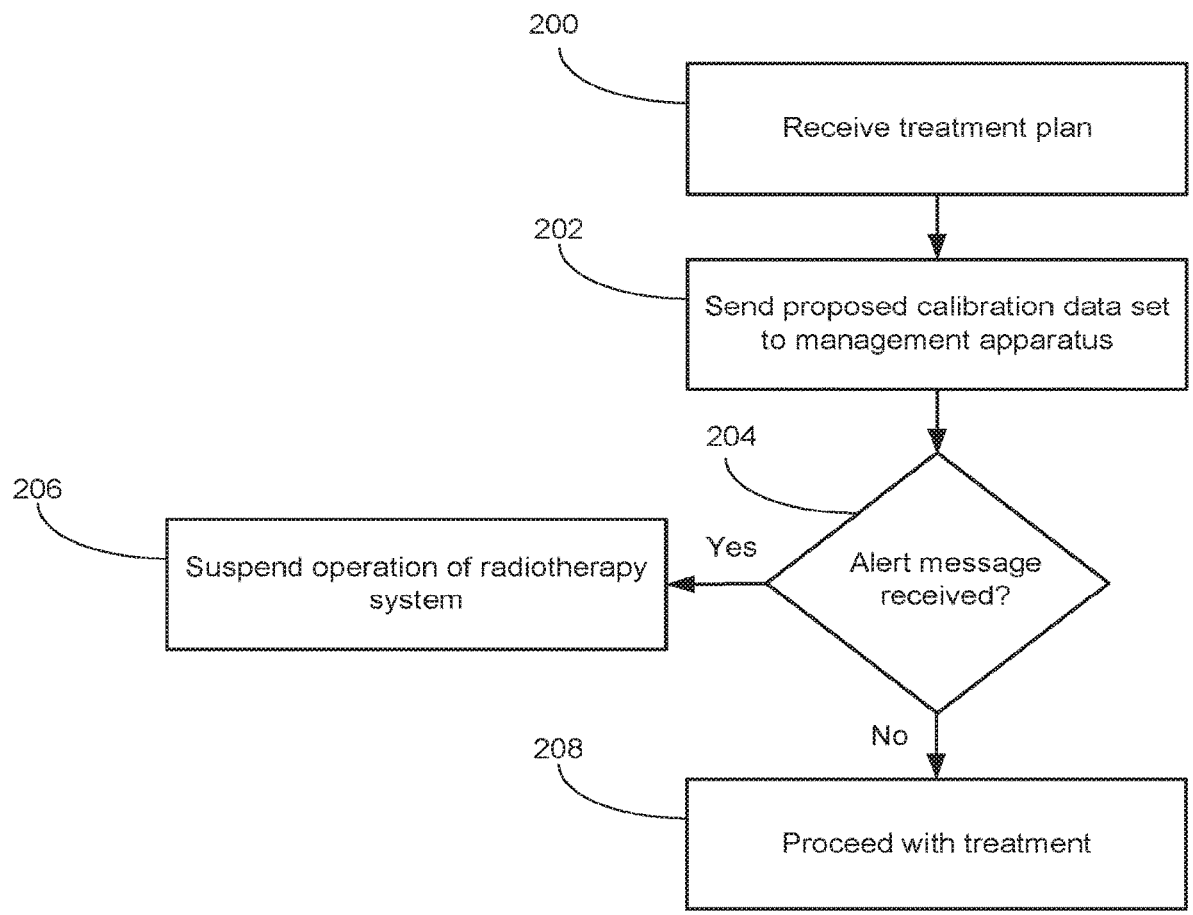
FIG. 3 is a flowchart of a method according to further embodiments of the present disclosure.

FIG. 3 is a flowchart of a method according to embodiments of the present disclosure as performed by the control device 30. The method begins in step 200, where a treatment plan 32 is received from a treatment planning apparatus.

In step 202, prior to treatment, the calibration data set stored in memory of the control device 30 is sent to the management apparatus 12. In one embodiment the calibration data set is sent just prior to treatment, i.e. once the treatment plan 32 is loaded into the radiotherapy apparatus.

The management apparatus 12 compares the calibration settings of the calibration data set to the allowable ranges defined in its database 15, and transmits a message back to the radiotherapy system 18a, 18b. If one or more (or a predetermined number) of the proposed calibration settings falls outside its allowable range, an alert message is received in step 204 and the further operation of the radiotherapy system may be suspended in step 206. Otherwise, the treatment is allowed to proceed (step 208). The radiotherapy system 18a may receive a message to this effect from the management apparatus 12.

The present disclosure thus provides methods and apparatus for safely managing the provision of radiotherapy treatment potentially in many different locations around the world. A database is formed comprising allowable ranges for each of a plurality of calibration settings in a calibration data set used to implement treatment plans in radiotherapy systems. Prior to treatment, the calibration settings of a proposed calibration data set are compared to these allowable ranges to see whether the treatment should be allowed to proceed. If one or more of the proposed calibration settings falls outside the allowable ranges, the therapy session may be stopped or prevented altogether.

Those skilled in the art will appreciate that various amendments and alterations can be made to the embodiments described above without departing from the scope of the disclosure as defined in the claims appended hereto.

What is claimed is:

1. A computer-implemented method comprising the following operations performed by one or more processors:
   loading a treatment plan for implementation by a radiotherapy system;
   receiving calibration settings for a plurality of operational components of the radiotherapy system, wherein:
      the calibration settings are received prior to implementation of the treatment plan by the radiotherapy system, and
      the calibration settings are used by the radiotherapy system to translate the treatment plan into instructions for the plurality of operational components;
   comparing the calibration settings for the radiotherapy system with allowable ranges of the calibration settings associated with the plurality of operational components;
   generating an alert signal based on whether a subset of the calibration settings for the radiotherapy system falls outside the allowable ranges; and
   transmitting the alert signal to the radiotherapy system prior to implementation of the treatment plan by the radiotherapy system.

2. The method according to claim 1, wherein the alert signal comprises instructions to suspend operation of the radiotherapy system.

3. The method according to claim 1, wherein the alert signal comprises a message for display at the radiotherapy system.

4. The method according to claim 1, wherein the operational components comprise two or more of: a rotatable gantry, a source of therapeutic radiation for generating a beam of radiation, a beam monitor device, or a collimator for collimating the beam of radiation.

5. The method according to claim 1, wherein the treatment plan comprises one or more parameters defining one or more of:
   an amount of radiation to be delivered by the radiotherapy system;
   an angle from which radiation is to be delivered; or
   a shape of a radiation beam.

6. The method according to claim 1, further comprising:
   allowing the radiotherapy system to implement the treatment plan when the subset of the calibration settings for the radiotherapy system falls within the allowable ranges.

7. The method according to claim 1, wherein the subset of calibration settings for the radiotherapy system comprises a user-defined number of calibration settings.

8. The method according to claim 1, wherein receiving the calibration settings comprises receiving the calibration settings during the step of loading the treatment plan.

9. The method according to claim 1, further comprising:
storing the allowable ranges of the calibration settings in a database of calibration data sets.

10. The method according to claim 9, wherein the calibration data sets comprise calibration settings for a plurality of treatment plans implemented by the radiotherapy system.

11. The method according to claim 10, further comprising:
deriving the allowable ranges from the calibration data sets; and
storing the derived allowable ranges in the database.

12. The method according to claim 11, further comprising:
updating the database with the calibration settings for the radiotherapy system when the subset of the calibration settings falls within the allowable ranges of values.

13. A non-transitory computer-readable storage medium storing code which, when executed by one or more processors, causes the one or more processors to:
load a treatment plan for implementation by a radiotherapy system;
receive calibration settings for a plurality of operational components of the radiotherapy system, wherein:
the calibration settings are received prior to implementation of the treatment plan by the radiotherapy system, and
the calibration settings are used by the radiotherapy system to translate the treatment plan into instructions for the plurality of operational components;
compare the calibration settings for the radiotherapy system with allowable ranges of the calibration settings associated with the plurality of operational components;
generate an alert signal based on whether a subset of the calibration settings for the radiotherapy system falls outside the allowable ranges; and
transmit the alert signal to the radiotherapy system prior to implementation of the treatment plan by the radiotherapy system.

14. A radiotherapy management apparatus comprising:
a storage device storing instructions; and
one or more processors coupled to the storage device and executing the instructions to perform operations comprising:
loading a treatment plan for implementation by a radiotherapy system;
receiving calibration settings for a plurality of operational components of the radiotherapy system, wherein:
the calibration settings are received prior to implementation of the treatment plan by the radiotherapy system, and
the calibration settings are used by the radiotherapy system to translate the treatment plan into instructions for the plurality of operational components;
comparing the calibration settings for the radiotherapy system with allowable ranges of the calibration settings associated with the plurality of operational components;
generating an alert signal based on whether a subset of the calibration settings for the radiotherapy system falls outside the allowable ranges; and
transmitting the alert signal to the radiotherapy system prior to implementation of the treatment plan by the radiotherapy system.

15. The radiotherapy management apparatus according to claim 14, wherein the alert signal comprises instructions to suspend operation of the radiotherapy system.

16. The radiotherapy management apparatus according to claim 14, wherein the operations further comprise:
allowing the radiotherapy system to implement the treatment plan when the subset of the calibration settings for the radiotherapy system falls within the allowable ranges.

17. The radiotherapy management apparatus according to claim 14, wherein receiving the calibration settings comprises receiving the calibration settings during the step of loading the treatment plan.

18. The radiotherapy management apparatus according to claim 14, wherein the operations further comprise:
storing the allowable ranges of the calibration settings in a database of calibration data sets, the calibration data sets comprising calibration settings for a plurality of treatment plans implemented by the radiotherapy system.

19. The radiotherapy management apparatus according to claim 18, wherein the operations further comprise:
deriving the allowable ranges from the calibration data sets; and
storing the derived allowable ranges in the database.

20. The radiotherapy management apparatus according to claim 19, wherein the operations further comprise:
updating the database with the calibration settings for the radiotherapy system when the subset of the calibration settings falls within the allowable ranges of values.

* * * * *